United States Patent
Foncubierta Rodriguez et al.

(10) Patent No.: US 11,830,622 B2
(45) Date of Patent: Nov. 28, 2023

(54) PROCESSING MULTIMODAL IMAGES OF TISSUE FOR MEDICAL EVALUATION

(71) Applicant: International Business Machines Corporation, Armonk, NY (US)

(72) Inventors: Antonio Foncubierta Rodriguez, Zurich (CH); Pushpak Pati, Zurich (CH); Guillaume Jaume, Zurich (CH); Kevin Thandiackal, Gattikon (CH)

(73) Assignee: International Business Machines Corporation, Armonk, NY (US)

( * ) Notice: Subject to any disclaimer, the term of this patent is extended or adjusted under 35 U.S.C. 154(b) by 431 days.

(21) Appl. No.: 17/346,195

(22) Filed: Jun. 11, 2021

(65) Prior Publication Data

US 2022/0399114 A1    Dec. 15, 2022

(51) Int. Cl.
    *G16H 50/20*        (2018.01)
    *G06T 7/30*         (2017.01)
    (Continued)

(52) U.S. Cl.
    CPC .............. *G16H 50/20* (2018.01); *G06T 7/13* (2017.01); *G06T 7/30* (2017.01); *G16H 10/40* (2018.01);
    (Continued)

(58) Field of Classification Search
    CPC . G06T 2207/10056; G06T 2207/20016; G06T 2207/20072; G06T 2207/20081;
    (Continued)

(56) References Cited

U.S. PATENT DOCUMENTS 9,710,695 B2    7/2017    Xu
2010/0240996 A1*    9/2010    Ionasec .................. G06T 7/262
                                                                 600/443
(Continued)

FOREIGN PATENT DOCUMENTS

WO     2019110561 A1    6/2019

OTHER PUBLICATIONS

Guillaume Jaume,"Towards Explainable Graph Representations in Digital Path," Jul. 1, 2020, Computer Vision and Pattern Recognition,arXiv:2007.00311v1 [cs.CV], pp. 11-14.*
(Continued)

*Primary Examiner* — Omar S Ismail
(74) *Attorney, Agent, or Firm* — Richard B. Thomas

(57) ABSTRACT

Methods and systems are provided for processing different-modality digital images of tissue. The method includes, for each image, detecting biological entities in the image and generating an entity graph comprising entity nodes, representing respective biological entities, interconnected by edges representing interactions between entities represented by the entity nodes. The method also includes selecting, from each image, anchor elements comprising elements corresponding to anchor elements of at least one other image, and generating an anchor graph in which anchor nodes, representing respective anchor elements, are interconnected with entity nodes of the entity graph for the image by edges indicating relations between entity nodes and anchor nodes. The method further includes generating a multimodal graph by interconnecting anchor nodes of the anchor graphs for different images via correspondence edges indicating correspondence between anchor nodes, and processing the multimodal graph to output multimodal data, derived from the plurality of images, for medical evaluation.

20 Claims, 6 Drawing Sheets

(51) Int. Cl.
  *G06T 7/13* (2017.01)
  *G16H 10/40* (2018.01)
  *G16H 70/60* (2018.01)
  *G16H 30/00* (2018.01)
(52) U.S. Cl.
  CPC .............. *G16H 30/00* (2018.01); *G16H 70/60* (2018.01); *G06T 2207/30024* (2013.01)
(58) Field of Classification Search
  CPC ......... G06T 2207/30024; G06T 7/0012; G06T 7/13; G06T 7/30; G06T 7/344; G16H 10/40; G16H 30/00; G16H 50/20; G16H 70/60
  See application file for complete search history.

(56) References Cited

U.S. PATENT DOCUMENTS

| | | | |
|---|---|---|---|
| 2013/0230220 A1 | 9/2013 | Yu | |
| 2017/0091937 A1 | 3/2017 | Barnes | |
| 2018/0289443 A1* | 10/2018 | Wade | A61B 1/000095 |
| 2019/0090976 A1* | 3/2019 | Wade | G16H 40/63 |
| 2020/0152289 A1* | 5/2020 | Cleary | G16B 25/10 |
| 2020/0302603 A1* | 9/2020 | Barnes | G06T 7/162 |
| 2021/0073986 A1* | 3/2021 | Kapur | G06T 7/11 |
| 2021/0103757 A1* | 4/2021 | Jang | G06F 18/25 |
| 2021/0103797 A1* | 4/2021 | Jang | G06V 30/19173 |
| 2021/0113172 A1* | 4/2021 | Huang | A61B 6/5217 |
| 2021/0183514 A1* | 6/2021 | Muehlberg | G06T 7/0016 |
| 2021/0201111 A1* | 7/2021 | Laszlo | G06N 3/086 |
| 2021/0287363 A1* | 9/2021 | Bhatia | G06T 3/60 |

OTHER PUBLICATIONS

Kaustav Bera, "Artificial intelligence in digital pathology—new tools for diagnosis and precision oncology," Aug. 9, 2019, Nature Reviews Clinical Oncology,vol. 16, Nov. 2019,pp. 703-711.*
Harshita Sharma, "A review of graph-based methods for image analysis in digital histopathology," Aug. 2015,The official Journal of the European Society of Digital & Integrative Pathology, 2015, pp. 6-16.*
Mohammed Adnan, "Representation Learning of Histopathology Images using Graph Neural Networks," Jun. 2020, Proceedings of the IEEE/CVF Conference on Computer Vision and Pattern Recognition (CVPR) Workshops, 2020, pp. 1-6.*
Joshua Levy,"Topological Feature Extraction and Visualization of Whole Slide Images using Graph Neural Networks," Jan. 3-7, 2021, Pacific Symposium on Biocomputing 2021, pp. 288-293.*
International Application No. PCT/EP2022/065606. Notification of Transmittal of the International Search Report and the Written Opinion of the International Searching Authority, or the Declaration, dated Oct. 17, 2022. (12 pages).
Pati, P., Jaume, G., Fernandes, L.A., Foncubierta, A., Feroce, F., Anniciello, A.M., Scognamiglio, G., Brancati, N., Riccio, D., Bonito, M.D., Pietro, G.D., Botti, G., Goksel, O., Thiran, J., Frucci, M., & Gabrani, M. (2020). HACT-Net: A Hierarchical Cell-to-Tissue Graph Neural Network for Histopathological Image Classification. ArXiv, abs/2007.00584.
Pati, P., Jaume, G., Foncubierta, A., Feroce, F., Anniciello, A.M., Scognamiglio, G., Brancati, N., Fiche, M., Dubruc, E., Riccio, D., Bonito, M.D., Pietro, G.D., Botti, G., Thiran, J., Frucci, M., Goksel, O., & Gabrani, M. (2021). Hierarchical graph representations in digital pathology. Medical image analysis, 75, 102264.
Sharma, H., Zerbe, N., Lohmann, S., Kayser, K., Hellwich, O., & Hufnagl, P. (2015). A review of graph-based methods for image analysis in digital histopathology. Diagnostic Pathology, 1.
Adnan et al., "Representation Learning of Histopathology Images using Graph Neural Networks," 2020 IEEE/CVF Conference on Computer Vision and Pattern Recognition Workshops (CVPRW), Jun. 14-19, 2020, vol. 1, pp. 4254-4261. < https://www.computer.org/csdl/proceedings-article/cvprw/2020/09150728/1lPHe1S5DIS>.
Bera et al., "Artificial intelligence in digital pathology—new tools for diagnosis and precision oncology," Nature Reviews Clinical Oncology, vol. 16, Aug. 9, 2019, pp. 703-715. <https:/pubmed.ncbi.nlm.nih.gov/31399699/>.
Jaume et al., "Towards Explainable Graph Representations in Digital Pathology," ICML 2020 Workshop on Computational Biology (WCB), Jul. 2020, 5 pages. <https://www.researchgate.net/publication/342622666_Towards_Explainable_Graph_Representations_in_Digital_Pathology>.
Lange et al., "Pathology AI (Artificial Intelligence) Reference Guide," Flagship Biosciences Inc., accessed Jun. 8, 2021, 17 pages. <https://digitalpathologyassociation.org/_data/cms_files/files/PathologyAI_ReferencGuide.pdf>.
Levy et al., "Topological Feature Extraction and Visualization of Whole Slide Images using Graph Neural Networks," bioRxiv, Aug. 3, 2020, 13 pages. <https://www.biorxiv.org/content/10.1101/2020.08.01.231639v1.full.pdf>.
Saafin et al., "Image Fusion Of Unregistered Colour Digital Pathology Images," Irish Machine Vision and Image Processing Conference, Aug. 2017, 8 pages. <https://www.researchgate.net/publication/320100925_IMAGE_FUSION_OF_UNREGISTERED_COLOUR_DIGITAL_PATHOLOGY_IMAGES>.

* cited by examiner

Anchor Graph

Multimodal Graph

Anchors (superpixels)

Anchor Graph

PROCESSING MULTIMODAL IMAGES OF TISSUE FOR MEDICAL EVALUATION

BACKGROUND

The present invention relates generally to processing multimodal images of tissue for medical evaluation. Computer-implemented methods are provided for processing a plurality of different-modality digital images of tissue, together with systems and computer program products implementing such methods.

Diagnosis and treatment planning for various diseases is based on analysis of digital images of disease tissue. Images can be produced using various techniques, resulting in images with different image-modalities. Medical evaluation is often based on analysis of multimodal images, i.e., two or more different-modality images, of the tissue. Digital pathology, for instance, involves analyzing digital images of slides containing tissue specimens, such as slices of a tumor biopsy, which are typically treated with different stains, e.g., different biomarkers, to highlight specific tissue parts. Visual inspection can be performed through a screen that renders the so-called "whole-slide image" (WSI) of a tissue specimen for each of the different stains. A WSI is a digitized microscopy image taken at multiple different magnification levels, allowing analysis of specimens from macroscopic to microscopic level. Given the tissue heterogeneity, tissue polymorphism and the large amount of data contained in such images, this task is tedious, time-consuming and prone to inter- and intra-observer variability. Moreover, the image content of multimodal images is generally not aligned. For example, alignment between differently-stained pathology slides can vary due to slicing or other manipulation of the tissue. This presents a further complication for multimodal image analysis.

One technique for coping with the alignment issue involves independent analysis of the different-modality images, with analysis results being combined at some stage to produce a final diagnosis. Relevant data is extracted from each image by independent examination of image features. A decision (e.g., whether tissue is diseased or healthy, or whether a particular biomarker is expressed) can be made for each image independently, and the individual decisions are then combined to obtain a final diagnosis. Alternatively, the feature data from individual images can be aggregated and processed altogether to produce a final decision. AI (Artificial Intelligence) can be exploited in these decision processes. For example, machine learning models can be trained to detect cells in stained tissue samples and classify cells as healthy or diseased based on attributes such as size, shape, color, cell distribution, and so on.

The above techniques, based on fusion of independently extracted information from different-modality images, cannot capture spatial or other information in context across the multimodal images if the images are not aligned. Image registration techniques can be employed to transform images into alignment, but fine-grained registration of tissue can distort the appearance of biological entities such as cells, thus changing vital information in irreversible ways. Compute-intensity of image registration also depends heavily on image complexity. While registration of an MRI (Magnetic Resonance Imaging) and a CT (Computerized Tomography) image may take 15 minutes, WSI images have multi-gigapixel resolution, making registration extremely costly in terms of computation. In addition, registration is more difficult if images, such as differently-stained pathology slides, do not highlight the same structures (nuclei, cells, cytoplasm, membrane, etc).

SUMMARY

One aspect of the present invention provides a computer-implemented method for processing a plurality of different-modality digital images of tissue. The method includes, for each image, detecting biological entities in the image and generating an entity graph comprising entity nodes, the entity nodes representing respective biological entities, interconnected by edges representing interactions between the biological entities represented by the entity nodes. The method selects, from each image, a set of anchor elements comprising elements corresponding to anchor elements of at least one other image, and generates an anchor graph in which anchor nodes, representing the respective anchor elements, are interconnected with the entity nodes of the entity graph for the image by the edges indicating relations between the entity nodes and the anchor nodes. The method further comprises generating a multimodal graph by interconnecting the anchor nodes of the anchor graphs for different images via correspondence edges indicating correspondence between the anchor nodes, and processing the multimodal graph to output multimodal data, derived from the plurality of images, for medical evaluation.

Methods embodying the invention process multimodal images of tissue to generate a multimodal graph representation in which nodes of anchor graphs, generated from individual image modes, are interconnected to indicate correspondence between anchor nodes of different-modality anchor graphs. Each anchor graph is constructed from an entity graph representing detected biological entities, and interactions between entities, in a particular image, and thus encodes relevant information in that image modality. Anchor elements (which may comprise biological entities and/or other image features explained below) are then selected such that corresponding anchor elements for different images provide a basis for construction of the multimodal graph in which anchor elements are interconnected by correspondence edges. The resulting multimodal graph can encode not only all relevant information from the individual image modalities, but also how this information relates to information in other modalities. Spatial and other correspondence information across multimodal images provides context for image interpretation, and this context is extremely valuable for medical evaluation. For example, many important patterns in digital pathology images (and other image modalities) are local, so the ability to extract local information across multiple modalities is medically significant. Methods embodying the invention allow multimodal data to be extracted in a context-aware manner from multiple image modalities, without the need for image registration, while preserving all unimodal information from individual images. This elegant technique thus offers more comprehensive and reliable evaluation of multimodal images for medical diagnosis. Moreover, the technique scales easily with image complexity, accommodating even whole-slide images, offering compact representations which can be efficiently processed for medical evaluation.

Embodiments may be applied to multimodal images of various types, including CT, MRI, Xray, etc., images produced by medical imaging techniques performed on a patient, as well as digital pathology images of tissue specimens from patients. The invention can be applied to particular advantage where one or more of the images is a digital pathology image in view of the large amount of detailed information contained in these microscopy images. In preferred embodiments, the different-modality images comprise digital pathology images of a tissue specimen with different stains. Each digital pathology image may comprise one or more component images, corresponding to respective magnification levels of a WSI, up to a complete WSI. For example, entity graphs may be hierarchical graphs in some embodiments, allowing entities at different hierarchy levels in an image, e.g., entities detected at multiple magnification levels of a WSI, to be readily accommodated.

Embodiments may be envisaged where insertion of correspondence edges in the multimodal graph follows directly from selection of the anchor elements, for example where the same or similar elements are selected as anchors in each image. Advantageously, however, an anchor graph includes, for each anchor node, a set of attributes associated with the corresponding anchor element. Correspondence edges can then be defined in the multimodal graph in dependence on attributes of the anchor elements for the different images. For example, correspondence edges between anchor nodes can be defined (at least partially) in dependence on similarity of the attributes for those anchor nodes. Alternatively, or in addition, correspondence edges between anchor nodes may be defined (at least partially) in dependence on graph edit distance between subgraphs, depending from those anchor nodes, in the anchor graphs. These and other techniques for defining correspondence edges will be explained further below.

Embodiments may also exploit image transformation techniques in the process of defining correspondence edges. In particular, some embodiments can select a reference modality for the images, and digitally transform each non-reference-modality image into a transformed image in the reference modality. Anchor elements for each non-reference modality image are mapped to its transformed image in the reference modality. For each anchor element in images in the reference modality, a set of attributes associated with that element in the reference modality image can be determined. Correspondence edges can then be defined (at least partially) in dependence on attributes of anchor elements determined from the reference-modality images. Here, correspondences are established based on attributes determined in a common image modality, offering better assessment of similarity between anchor nodes in different images.

The multimodal graph can be processed in various ways to output multimodal data derived from the images. In preferred embodiments, the multimodal graph is supplied to a pre-trained machine learning model which is adapted to output multimodal result data corresponding to a medical diagnosis, such as a classification (e.g., diseased or healthy), grading (e.g., on a severity scale), or other such diagnosis for the tissue. Alternatively, or in addition, the multimodal graph can be stored in a graph database to which medical personnel can input search queries via a user interface. In response to input of a search query, these embodiments can search the graph database to retrieve multimodal data relating to the search query, and the search results can be displayed via the user interface. Particularly advantageous embodiments, detailed below, can selectively display the different-modality images via the user interface, and, in response to user-selection of an area of one image, retrieve from the graph database multimodal data relating to the selected area and also corresponding features, identified via the multimodal graph, from one or more other image modes.

Respective further aspects of the invention provide a computing system which is adapted to implement a method for processing different-modality images of tissue as described above, and a computer program product comprising a computer readable storage medium embodying program instructions, executable by a computing system, to cause the computing system to implement such a method.

Embodiments of the invention will be described in more detail below, by way of illustrative and non-limiting example, with reference to the accompanying drawings.

DETAILED DESCRIPTION

Figure 1:
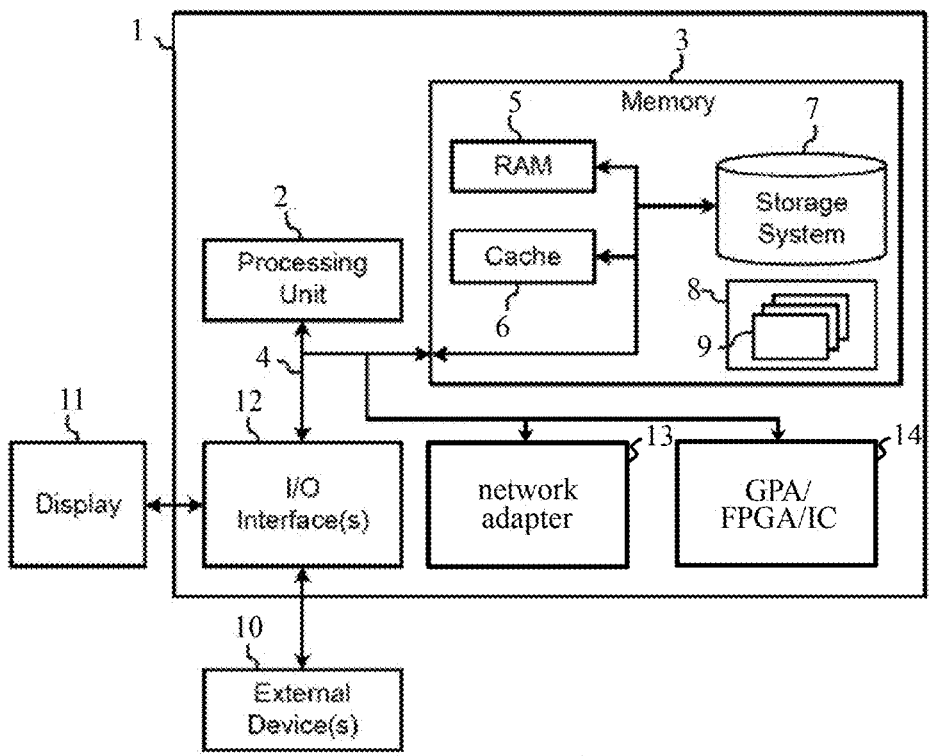
FIG. 1 is a schematic representation of a computing system for implementing methods embodying the invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments to be described can be performed as computer-implemented methods for processing multimodal digital images of tissue. The methods may be implemented by a computing system comprising one or more general- or special-purpose computers, each of which may comprise one or more (real or virtual) machines, providing functionality for implementing operations described herein. Steps of methods embodying the invention may be implemented by program instructions, e.g. program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

FIG. 1 is a block diagram of exemplary computing apparatus for implementing methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as one or more GPUs (graphics processing units), FPGAs, or integrated circuits (ICs), for implementing embodiments of the invention. It should be understood that other hardware and/or software components may be used in conjunction with computer 1. Examples include, but are not limited to: microcode, device drivers, redundant processing units, external disk drive arrays, RAID systems, tape drives, and data archival storage systems, etc.

Figure 2:
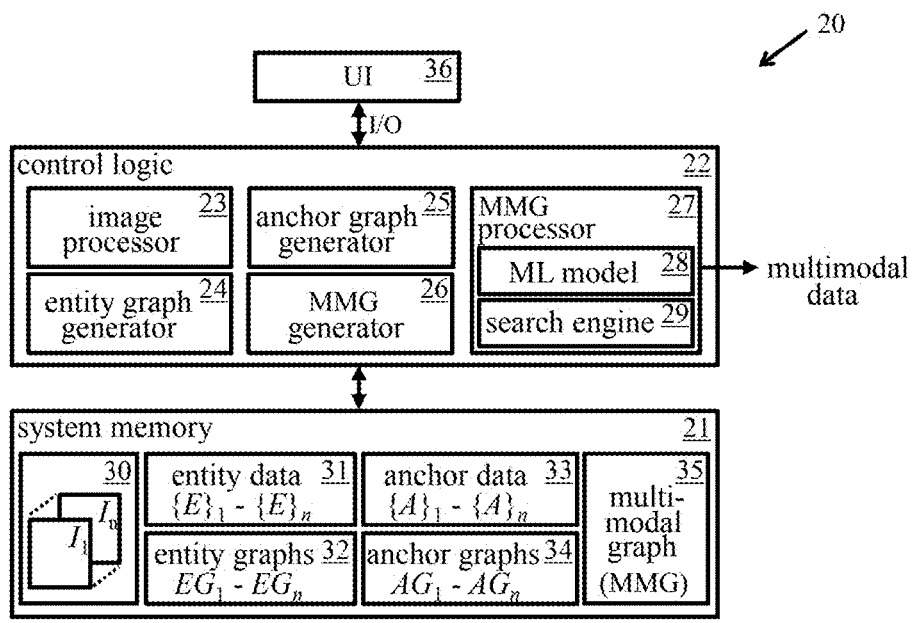
FIG. 2 illustrates component modules of a computing system for processing multimodal images of tissue.

The FIG. 2 schematic illustrates component modules of an exemplary computing system embodying the invention. The computing system 20 comprises memory 21 and control logic, indicated generally at 22, comprising functionality for processing multimodal digital images of tissue. Control logic 22 comprises an image processor module 23, an entity graph generator 24, an anchor graph generator 25, a multimodal graph (MMG) generator 26, and a graph processor module, i.e., a MMG processor 27 for processing a multimodal graph produced in operation of the system. In embodiments below, the MMG processor 27 may comprise one or both of a machine learning (ML) model 28 and a search engine 29.

Each of the logic modules 23 through 29 comprises functionality for implementing particular steps of a multimodal image processing method detailed below. These modules interface with memory 21 which stores various data structures used in operation of system 20. These data structures comprise: an image set 30 comprising a plurality n of different-modality tissue images denoted by $I_i$, i=1 to n; entity data 31 comprising a set of entity data $\{E\}_i$ for each image $I_i$; a set 32 of entity graphs $EG_i$ for respective images $I_i$; anchor data 33 comprising a set of anchor data $\{A\}_i$ for each image $I_i$; a set 34 of anchor graphs $AG_i$ for respective images $I_i$; and a multimodal graph 35. One or more I/O channels provide for communication between control logic 22 and operators/users of the system via a user interface (UI) 36 provided at one or more user computers which may be local or remote from system 20.

In general, functionality of logic modules 23 through 29 may be implemented by software (e.g., program modules) or hardware or a combination thereof. Functionality described may be allocated differently between system modules in other embodiments, and functionality of one or more modules may be combined. The component modules of system 20 may be provided in one or more computers of a computing system. For example, all modules may be provided in a user computer 1, or modules may be provided in one or more computers/servers to which user computers can connect via a network for input and analysis of multimodal images. Such a network may comprise one or more component networks and/or internetworks, including the Internet. System memory 21 may be implemented by one or memory/storage components associated with one or more computers of computing system 20.

Figure 3:
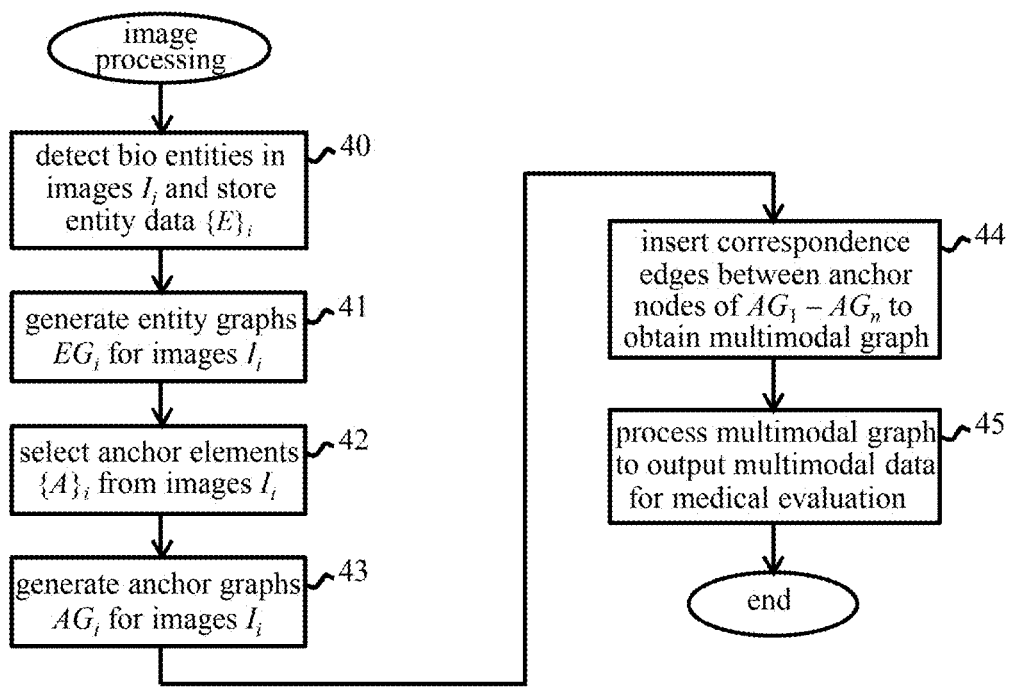
FIG. 3 indicates steps of a multimodal image processing method embodying the invention.

In operation of system 20, the images $I_1$ to $I_n$ are input to the system and stored at 30 in system memory 21. Basic steps of the subsequent image processing method are indicated in FIG. 3. In step 40 of this figure, the image processor 23 processes each image $I_i$ to detect biological (bio) entities in the image. The entities (e.g., nuclei, cells, tissue parts, etc.,) to be detected depend on the specific evaluation task to be performed for the tissue and can be identified by generally known image processing techniques. For identified entities, image processor 23 makes measurements in the image to determine locations of the entities and preferably also other attributes, described below, relating to form and distribution of entities. The resulting sets of entity data $\{E\}_1$ to $\{E\}_n$ for the images are stored at 31 in system memory 21.

In step 41, the entity graph generator 24 generates an entity graph $EG_i$ for each image $I_i$. An entity graph $EG_i$ comprises entity nodes, representing respective biological entities defined by entity data $\{E\}_i$ for image $I_i$, interconnected by edges representing interactions between entities represented by the entity nodes. Next, in step 42, the anchor graph generator 25 selects a set of anchor elements from each image $I_i$. As explained in more detail below, these anchor elements may comprise biological entities defined in $\{E\}_i$ and/or other features of the image $I_i$, and are selected such that the set of anchor elements for each image $I_i$ comprises elements corresponding to anchor elements of at least one other image $I_1$ to $I_n$. Anchor data $\{A\}_i$ defining the selected anchor elements for each image $I_i$ (and preferably attributes associated with these elements) is stored at 33 in system memory 21. In step 43, the anchor graph generator then generates a further graph, referred to herein as an anchor graph, for each image. The anchor graph $AG_i$ for an image $I_i$ contains anchor nodes, representing respective anchor elements defined in the anchor data $\{A\}_i$, which are interconnected with entity nodes of the entity graph $EG_i$ for that image. Edges interconnecting the entity and anchor nodes in this graph indicate relations between entity and anchor nodes as explained below. The resulting anchor graphs $AG_1$ to $AG_n$ are stored at 34 in system memory 21.

In step 44, the MMG generator 26 then generates a multimodal graph representing all the images $I_1$ to $I_n$. The multimodal graph is constructed by interconnecting anchor nodes of the anchor graphs for different images via edges (referred to herein as "correspondence edges") indicating correspondence between anchor nodes. These correspondence edges can be defined in various ways as explained below. The resulting multimodal graph 35 is stored in system memory 21. In step 45, the multimodal graph is processed by MMG processor 27 to output multimodal data, derived from the images $I_1$ to $I_n$ as encoded in the multimodal graph, for medical evaluation. Particular examples of this graph processing operation are described in detail below.

Figure 4:
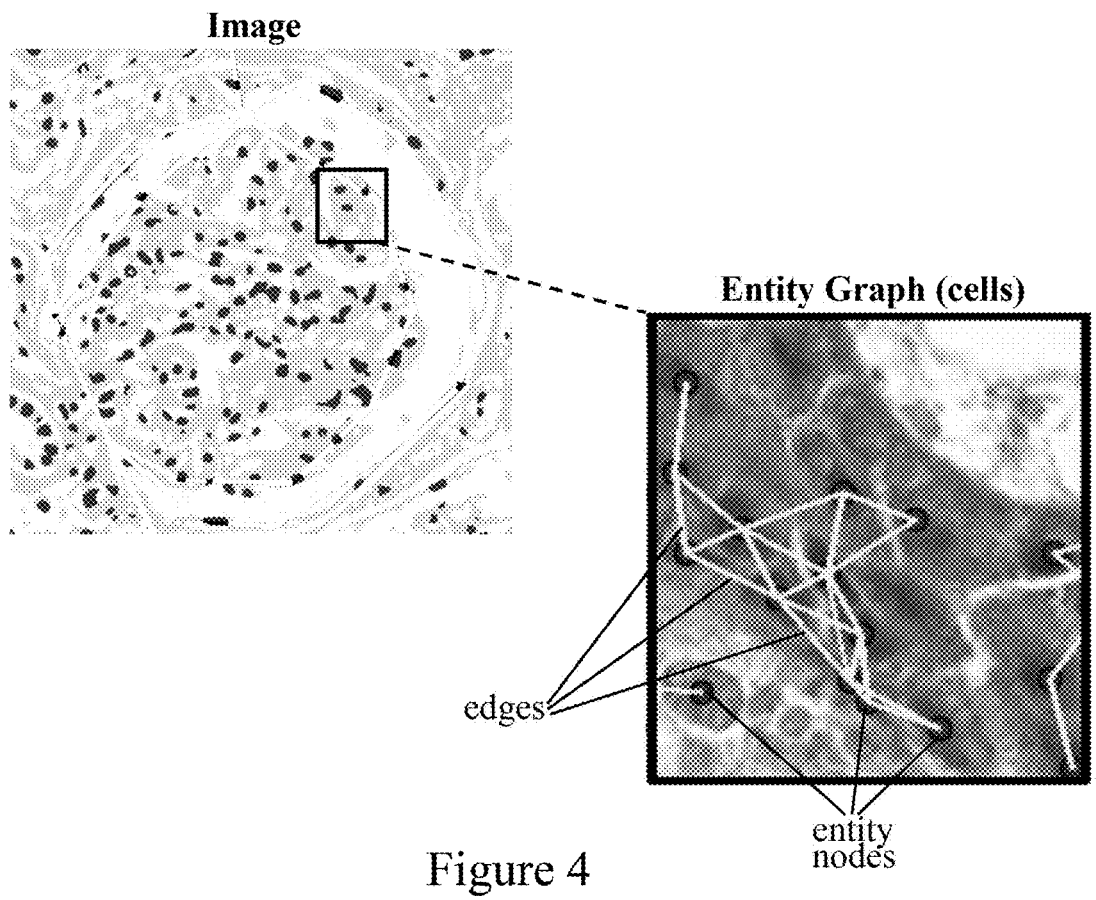
FIGS. 4, 5 and 6 illustrate principles of graph construction in an embodiment of the FIG. 3 method.

Entity graph construction in step 41 of FIG. 3 is illustrated schematically in FIG. 4. This example shows a digital pathology image, here of a cancer tumor, and the enlargement shows part of an entity graph superimposed on the image. Nodes of the entity graph are indicated by dark dots in the enlargement, and edges by white lines connecting pairs of entity nodes. In this example, nodes correspond to individual cells and edges correspond to cellular interactions. For each cell nucleus detected in the image, image processor 23 makes measurements to determine the location and other attributes of the cell. Cell location may be defined here by the spatial centroid of the nucleus. Other measured attributes may relate to shape, type, size, color, texture, and so on, of a cell. The resulting set of attributes for each entity can be defined by a vector (referred to herein as a "feature vector") of the measured features which is associated with the corresponding entity node in the graph. Edges representing interactions between the cells can be defined in dependence on distance between cells. For example, it can be assumed that spatially close cells encode biological interactions and should be connected by an edge in the graph, whereas distant cells have weak cellular interactions and should remain disconnected (no edge) in the graph. As a simple example, edges may be inserted between pairs of nodes representing cells within a predefined proximity threshold of each other. However, various other techniques can be envisaged for edge insertion as illustrated by examples below.

The entities represented in an entity graph may depend on the particular image modality and tissue type, and also on the magnification level of a digital pathology image. Entities may, for example, comprise one or more of nuclei, cells, tissue parts (e.g., epithelium, stroma, necrosis, lumen structures, muscle, fat, etc.), glands and whole tissues. Entities may be detected at different hierarchy levels, e.g., at each of a plurality of magnification levels in WSI. In some embodiments, the entity graph may be a hierarchical graph (described further below). Edges representing interactions between entities can be defined in various ways, and may depend on one or both of distance between entities and predetermined biological interactions between entities, e.g., based on pathological prior knowledge. Edges may also be weighted in some embodiments, with weights signifying degree or likelihood of interaction, e.g., based on distance/known interactions between entities. Attributes may include numerous other (handcrafted or learned) features as illustrated by examples below.

Anchor elements selected in step 42 of FIG. 3 may comprise particular entities in $\{E\}_i$ for an image and/or various other image features. For example, anchor elements may comprise biological entities at a different hierarchy level to those represented in the entity graph, e.g., tissue parts, glands, etc., which contain cells in a cell-level entity graph, or salient regions (i.e. regions which appear different to surrounding image regions) in the image. Any identifiable landmarks in the image, such as blood vessels, cavities, etc., may also be selected, as well as features based on additional processing of the image. For example, parts of the image may be segmented into so-called "superpixels" derived for the respective image as described further below. Grid-based techniques such as dense grid sampling may also be applied here. Such techniques apply some form of grid to an image and sample particular grid areas, e.g., pixel arrays, at defined locations. When selecting the set of anchor elements for a given image, the main objectives are to choose elements which can be related in some way to entities in the entity graph, and to include elements with some form of correspondence to anchor elements for one or more other images. An anchor element may be related to one or more bio entities from the same image by virtue of equivalence (anchor is entity or same type of entity), hierarchical correspondence (anchor contains entity) or positional correspondence or similarity (anchor at same location or contiguous with/close to entity) for example. The particular relations applied can be determined heuristically based on domain knowledge. Corresponding anchor elements in different images may also be defined in various ways. For example, selecting corresponding anchor elements in different images may comprise one or a combination of: selecting the same element (e.g., same landmark) in different images; selecting the same (or similar) type of element in each image; selecting elements at the same or similar locations (e.g., grid locations) in each image; and selecting elements with some known biological interaction or other association. Again, domain knowledge can be applied in the selection criteria here.

Figure 5:
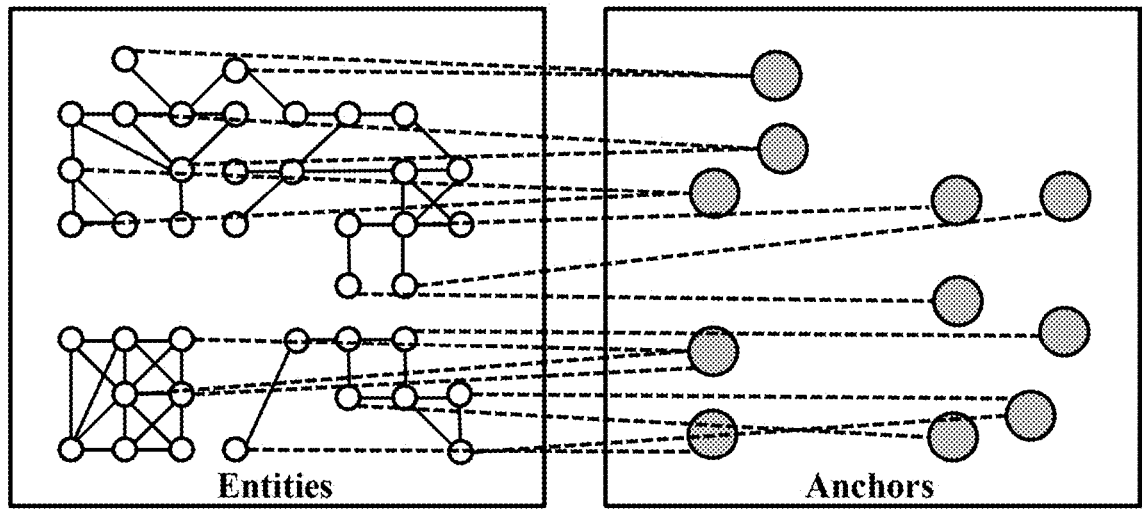

Anchor graph construction in step 43 of FIG. 3 is illustrated schematically in FIG. 5. An entity graph, with entity nodes interconnected by edges as described above, is shown on the left of the figure. Anchor nodes, shaded grey, are shown on the right. Node positions in the two squares represents approximate positions in the image in this representation. Edges shown by dashed lines interconnecting anchor nodes and entity nodes indicate positional and/or hierarchical relations between anchors and entities as described above. The anchor graph may also contain edges (not shown) between pairs of anchor nodes in some embodiments. Criteria for insertion of these inter-anchor edges can be similar to those for inter-entity edges described above.

For each anchor node in the anchor graph for an image, a set of attributes which are associated with the corresponding anchor element in the image can be defined in various ways. For example, anchor attributes may relate to type, location, appearance (size, shape, color, etc.) of an anchor element similarly to entity attributes described above. Alternatively, or in addition, anchor attributes may comprise attributes of related entities linked by anchor-entity edges to an anchor node in the anchor graph. Anchor attributes may also be determined from a digitally transformed image as explained below. The resulting set of attributes can be defined by a feature vector which is associated with the corresponding anchor node in the anchor graph.

Figure 6:
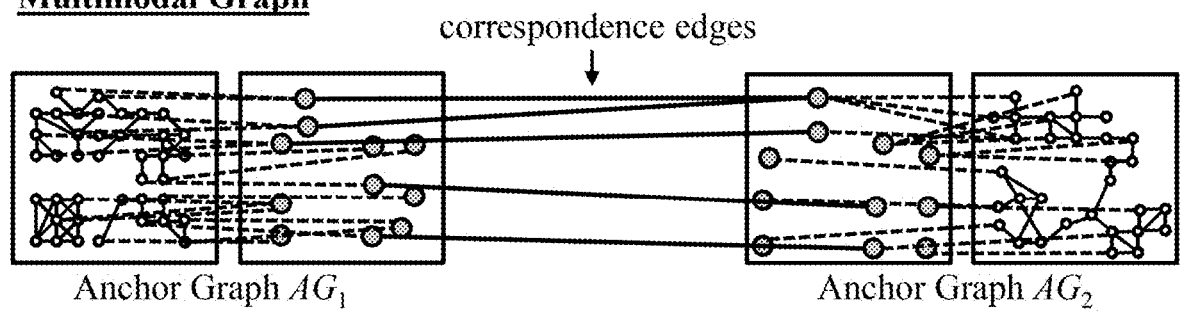

Multimodal graph construction in step 44 of FIG. 3 is illustrated schematically in FIG. 6. This shows MMG construction principles for anchor graphs $AG_1$ and $AG_2$ for two images I. The multimodal graph is generated by interconnecting anchor nodes of $AG_1$ and $AG_2$ via edges which indicate correspondence between the connected anchor nodes. Various techniques can be applied for insertion of these correspondence edges. In a simple embodiment, location of correspondence edges may follow directly from the criteria for selection of anchor elements in step 42 of FIG. 3, e.g., where the same elements, or elements at equivalent locations, are selected in each image. In preferred embodiments, however, correspondence edges are defined in dependence on attributes of the anchor elements for different images. For example, a correspondence edge can be defined between anchor nodes in dependence on similarity of the attributes for those anchor nodes. In particular, MMG generator 26 may compare the feature vectors for each pair of anchor nodes in $AG_1$ and $AG_2$ and insert a correspondence edge if the feature vectors, or predefined functions of these vectors, are sufficiently similar, e.g., differ by less than a threshold amount. As a simple example, a sum of the differences between equivalent attributes may be calculated and normalized over the number of attributes compared, and the result compared with a "similarity threshold" for insertion of a correspondence edge. Some or all attributes of the feature vectors may be compared here, and weighting may be applied to emphasize more important attributes, e.g., location, for assessing correspondence.

Alternatively, or in addition, the criterion for correspondence edge insertion may depend on features of the anchor graphs $AG_1$ and $AG_2$. For example, correspondence between a pair of anchor nodes may depend on graph edit distance between the subgraphs depending from those anchor nodes in their respective anchor graphs. Graph edit distance is a measure of the number of changes that have to be made to the subgraphs to obtain an identical subgraph. Correspondence or lack of correspondence between anchor nodes may be indicated by the presence or absence of an edge in the multimodal graph, and/or edges may be weighted with "correspondence weights" indicating degree of correspondence according to the assessment criteria.

Embodiments can also be envisaged in which correspondence edges are defined by supplying the anchor graphs for the images to a machine learning model which is pretrained to define correspondence edges between anchor nodes of such graphs. In particular, machine learning models which accept graphs as input can be trained to process anchor graphs and learn the assignment of correspondence edges/correspondence weights, based on manually annotated labels for training sets of anchor graphs. For example, models based on graph neural networks (GNNS) can be designed to receive a set of anchor graphs with fully-connected edges between anchor nodes. Such a model can be trained via an iterative training process in which the model output, e.g., a classification (such as diseased or healthy), is compared with the training label, and the model parameters are iteratively updated to reduce the output error. In the course of this training process, the correspondence weights (which may be binary or take a range of values) can be learned as the model parameters are updated, for example in an attention layer of the network in which the attention weights are learned during training. Other models may use known link-prediction techniques, e.g., using multilayer perceptrons, to establish correspondence between anchor nodes. Particular implementations of such models will be readily apparent to those skilled in the art.

In general, one or a combination of the techniques described above can be employed for defining correspondence edges in an MMG. While FIG. 6 shows a MMG for two images, the principles extend readily to more than two images. Correspondence edges may be defined between anchor nodes of all pairs of anchor graphs. Alternatively, one graph may be selected as a reference (based on task-specific criteria), and correspondence edges defined between this graph and each of the others. Either way, the resulting multimodal graph encodes all relevant information from the individual image modalities and also, via the correspondence edges, how this information is related between modalities. The multimodal graph thus encodes context for the different image modalities, allowing multimodal data to be extracted in a context-aware manner.

Figure 7:
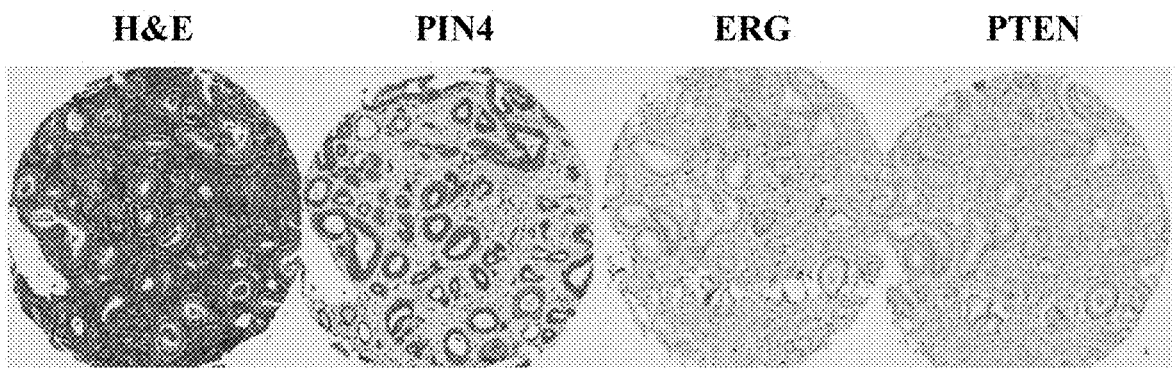
FIG. 7 shows digital pathology images with different stains.

An example of the above process is described in more detail below with reference to FIGS. 7 to 10 (as licensed under the Creative Commons Attribution 2.0 Generic license). FIG. 7 shows digital pathology images of a tissue specimen to which different stains have been applied. The first of these is an H&E (Haematoxylin and Eosin) stain. The others are histology stains for expression of different biomarkers, PIN4, ERG and PTEN. (While shown in black and white here, in color the H&E and PIN4 stains exhibit different shades of pink and purple, and ERG and PTEN stains show different shades of blue and brown). Image processor 23 may pre-process the WSIs for the specimen slides in generally known manner. Such preprocessing is task-specific (i.e., dependent on the particular evaluation to be performed for a given specimen) and involves standard processes such as stain normalization to remove staining variance across images, background removal, tissue area detection to bound regions of evaluation, and so on. By analyzing WSIs for the specimen slides at different magnification levels, entity and anchor graphs can be generated as described above. In this example, entity graphs represent cells, detected at high magnification, as illustrated in FIG. 4, and anchors are defined by superpixels generated from the same (or a lower-magnification) image in the WSI. Node attributes in the cell graphs include location, area, eccentricity, maximum and minimum length of axis, perimeter, solidity, and orientation of cells. Texture attributes include average foreground and background difference, standard deviation, skewness and mean entropy of intensity, as well as dissimilarity, homogeneity, energy and ASM (Active Shape Models) from a Gray-Level Co-occurrence Matrix as defined in "CGC-Net: Cell Graph Convolutional Network for Grading of Colorectal Cancer Histology Images", Y. Zhou et al., IEEE/CVF International Conference on Computer Vision Workshop, 2019. Edges in the cell graphs were obtained using a kNN (k-nearest neighbor) search to insert edges to the nearest neighbors of each cell, and then pruning edges longer than a distance threshold.

In each cell graph, presence or absence of an edge between entity nodes was defined by an N-by-N adjacency matrix with binary elements, where N is the number of entity nodes in the graph, and a "1" at position (p, q) in the matrix signifies an edge between node p and node q. The resulting entity graph is then fully defined by this adjacency matrix and a matrix of the feature vectors, described above, for respective nodes of the graph.

Figure 8:
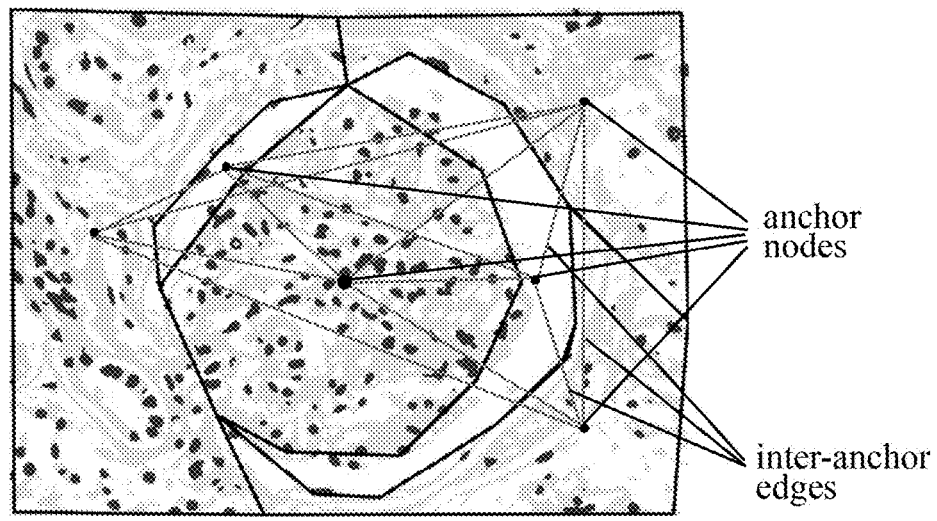
FIG. 8 shows an example of anchor elements for the FIG. 4 image.

An example of the superpixels (defining anchor elements represented by nodes of the anchor graphs) is illustrated in FIG. 8. This image was generated from the cell graph image of FIG. 4 using an SLIC (Simple Linear Iterative Clustering) algorithm (described in "Slic superpixels compared to state-of-the-art superpixel methods", R. Achanta et al., IEEE transactions on pattern analysis and machine intelligence, vol. 34, no. 11, pp. 2274-2282) emphasizing space proximity to over-segment tissue parts into non-overlapping homogeneous superpixels. To create superpixels capturing meaningful tissue information, adjacent similar superpixels were merged, where similarity was measured by various texture attributes such as contrast, dissimilarity, homogeneity, energy, and channel-wise color attributes (standard deviation, median, energy and skewness from an 8-bin color histogram). Anchor nodes in FIG. 8 were located at the spatial centroids of the superpixels. Inter-anchor edges were inserted between anchor nodes assuming that tissue parts represented by adjacent superpixels biologically interact and should be connected by edges. The large central node in this image depicts the centroid of the surrounding stroma tissue in the tumor. Superpixel attributes for anchor nodes included spatial location along with various color and texture features as for nodes of the cell graphs. Selected features were also applied to an ML model, here a RF (Random Forests) model pretrained to classify tissue parts by tissue type (here epithelium, stroma, necrosis, and background tissue) as an additional attribute.

Figure 9:
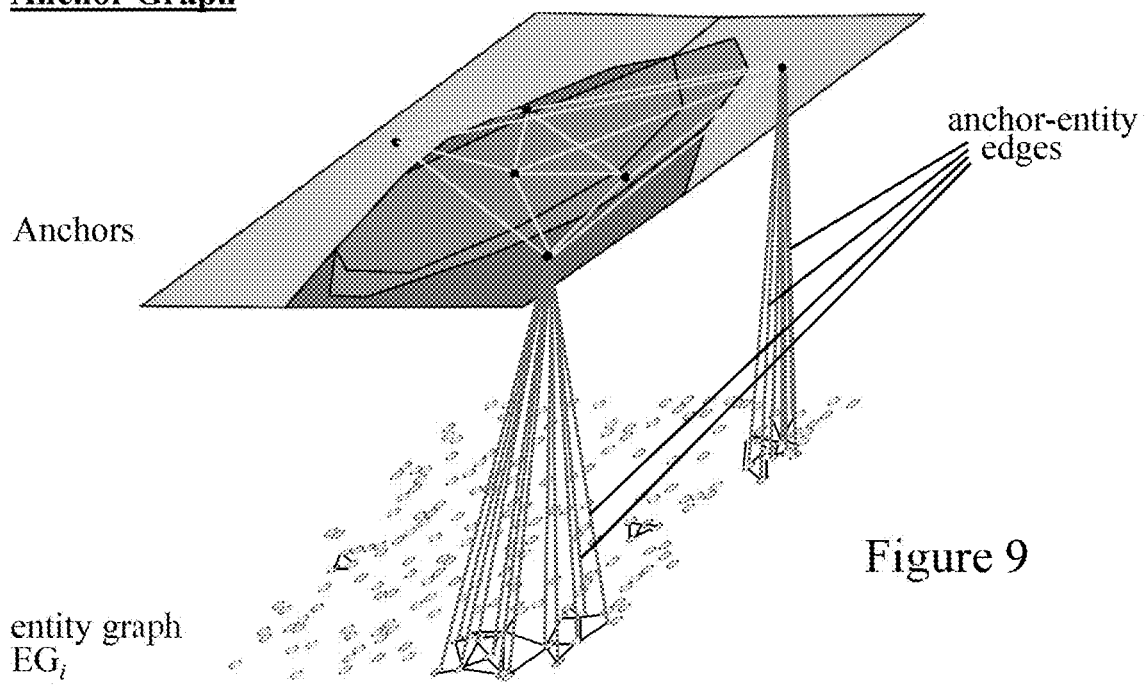
FIG. 9 illustrates construction of an anchor graph based on anchor elements of FIG. 8.

Anchor graphs for each image were generated as shown in FIG. 9. This illustrates anchor graph construction for the images of FIGS. 4 and 8. Anchor-entity edges were inserted based on positional correspondence of cells and superpixels. In particular, if the cell represented by a node in the cell graph spatially belongs to the tissue-part (superpixel) represented by an anchor node, then an anchor-entity edge is defined between these two nodes. The anchor graph is then defined by the underlying cell graph (cell feature matrix and inter-cell adjacency matrix), the matrix of anchor feature vectors and a binary adjacency matrix for the inter-anchor edges, and an additional adjacency matrix for the anchor-entity edges. In particular, anchor-entity edges can be defined by a binary assignment matrix of dimension $N_i$-by-$N_{i+1}$, where $N_i$ is the number of nodes in the cell graph, $N_{i+1}$ is the number of anchor nodes, and a "1" at position (p, q) in this matrix indicates an anchor-entity edge between a node p in the cell graph and an anchor node q.

Figure 10:
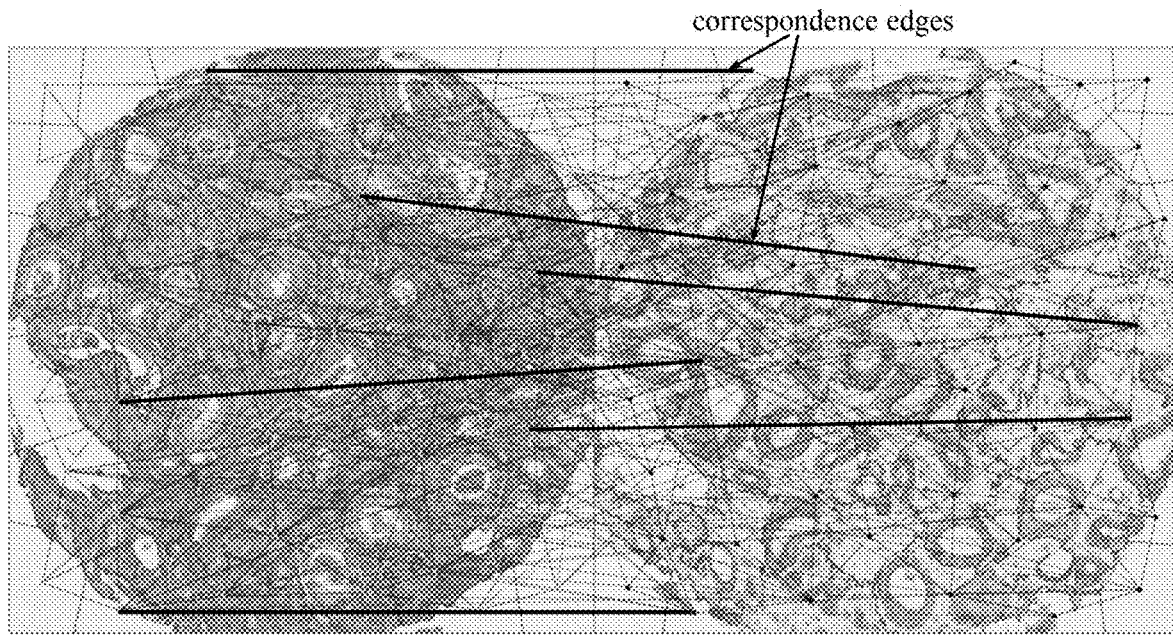
FIG. 10 illustrates correspondence edges of a multimodal graph for differently stained pathology images.

After generating the anchor graphs for the images, correspondence edges were inserted between superpixel anchors of the individual graphs as described above. FIG. 10 shows an example of correspondence edges between anchor nodes for two of the images (H&E and PIN4) of FIG. 7. Here, correspondence edges (some of which are highlighted in bold for clarity) were inserted based on similarity of superpixel attributes, including location and color/texture attributes. The resulting multimodal graph for the images is then fully defined by the anchor graph data for the constituent anchor graphs, and an additional set of MMG adjacency matrices. Each MMG adjacency matrix defines the correspondence edges between a pair of the constituent anchor graphs of the multimodal graph.

Figure 11:
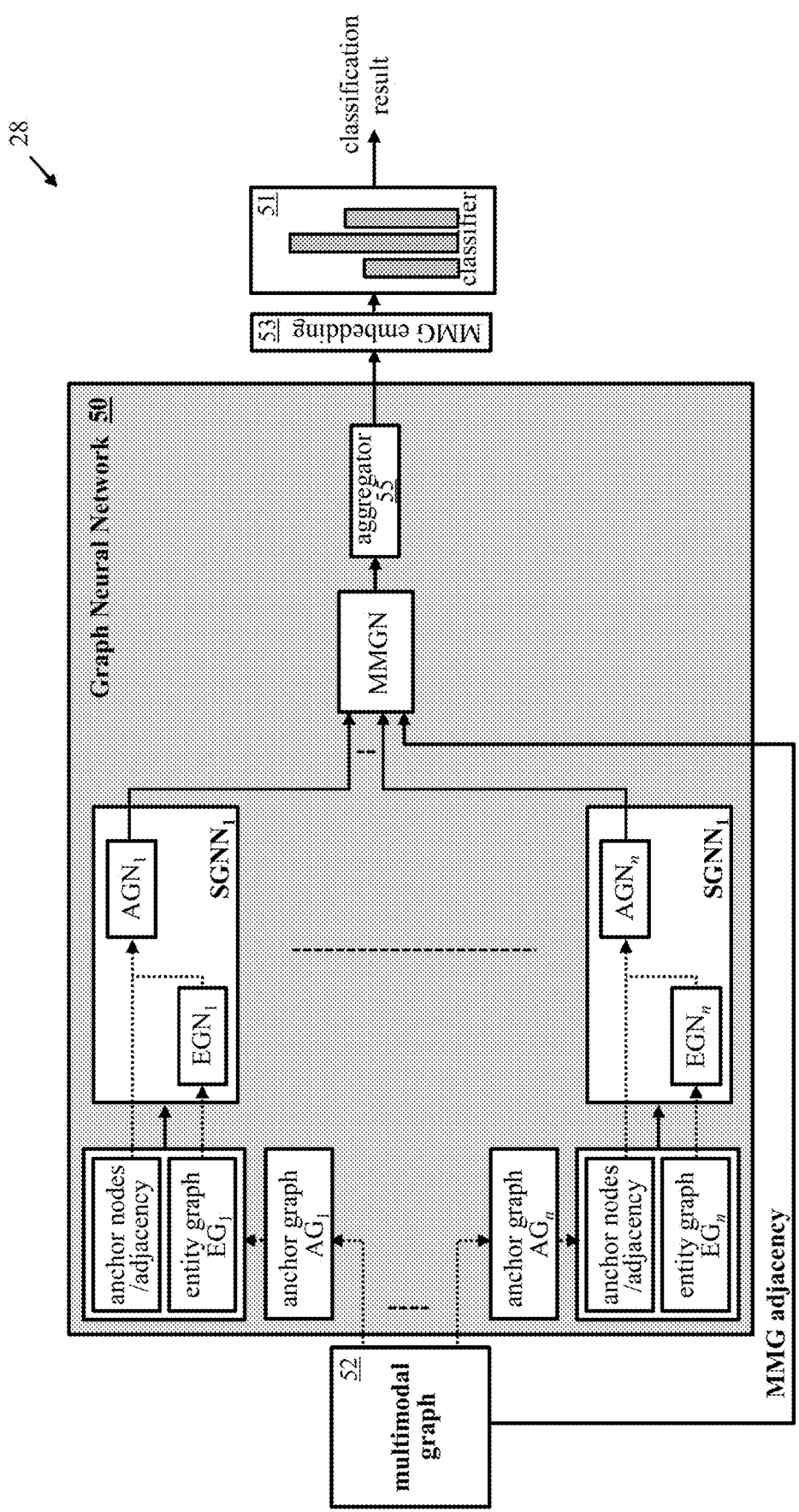
FIG. 11 illustrates architecture of a machine learning model for processing multimodal graphs in an embodiment of the system.

FIG. 11 illustrates architecture of an exemplary ML model 28 for processing the multimodal graph in MMG processor 27. The model 28 comprises a graph neural network 50 and an evaluator which is implemented here by an ML classifier 51. The graph neural network (GNN) 50 is adapted to process the MMG 52 for a set of images to produce embedded data representing the MMG, i.e., MMG embedding 53. Classifier 51 is adapted to map the data associated with the MMG embedding 53 to multimodal result data corresponding to a medical diagnosis (e.g., diseased or healthy, tumor-type, severity grading, etc.) for the tissue specimen. The ML model 28 can be pretrained in well-known manner to output the desired result data for a particular diagnostic task. In particular, the model can be trained via a supervised learning process in which a dataset of multimodal graphs, generated as described above from multimodal images which have been manually annotated with labels indicating the correct diagnosis, is supplied graph-by-graph to the model. As the training graphs are supplied to the model, errors between the model output and the training label are calculated and backpropagated through the network, and the model parameters are updated via an optimization process (e.g., a gradient descent method) so as to reduce the output error. The model is thus progressively updated until a convergence condition (e.g., a desired accuracy) is achieved. The trained model can then be applied for inference to new (previously unseen) graphs.

In operation of model 28, MMG 52 is supplied to GNN 50. The GNN 50 comprises a plurality of subgraph networks, labeled $SGNN_1$ to $SGNN_n$, for receiving respective anchor graphs $AG_1$ to $AG_n$ in the MMG. Model 28 may include multiple such SGNN modules, and a number of these are then used according to the number of anchor graphs in MMG 52. Each subgraph network $SGNN_i$ comprises an entity graph network $EGN_i$ and an anchor graph network $AGN_i$ as shown. Each of these networks $EGN_i$ and $AGN_i$ comprises a multilayer GNN which may be implemented, for example, by a message passing neural network. In this preferred embodiment, each network $EGN_i$ and $AGN_i$ comprises a Graph Isomorphism Network as described in "How powerful are graph neural networks?", K. Xu et al., International Conference on Learning Representations, ICLR, 2019. In each module $SGNN_i$, the entity graph network $EGN_i$ receives the graph data (feature matrix and adjacency matrix) for the entity graph $EG_i$ in the input anchor graph $AG_i$, and produces node embeddings for respective nodes of the entity graph. The node embeddings for $EG_i$ are then assigned to nodes of the anchor graph $AG_i$ by the following anchor graph network $AGN_i$. In particular, $AGN_i$ receives the anchor node feature matrix and the inter-anchor adjacency matrix, and also the assignment matrix defining the anchor-entity edges in the anchor graph. The anchor graph network $AGN_i$ assigns the node embeddings produced by $EGN_i$ to anchor nodes along the anchor-entity edges defined by the assignment matrix. Node embeddings assigned to a given anchor node are added to (e.g., concatenated or otherwise combined with) the input feature vector for that anchor node. The anchor graph network $AGN_i$ then produces node embeddings for the anchor nodes. The resulting anchor node embeddings thus embed all information in the anchor graph $AG_i$.

The node embeddings for the individual anchor graphs $AG_i$ are then supplied to a further GNN, labeled MMGN, which also receives the MMG adjacency matrices defining correspondence edges between anchor nodes of the different anchor graphs. MMGN then produces the final node embeddings for all anchor nodes in the multimodal graph. The resulting node embeddings output by MMGN are then aggregated (e.g., concatenated or otherwise combined) in an aggregator module 55 to produce the final MMG embedding 53 representing the multimodal graph. The MMG embedding 53 is supplied to classifier 51 to obtain the classification result for the MMG as a whole. This multimodal classification result is then output by MMG processor 27 for medical evaluation.

Figure 12:
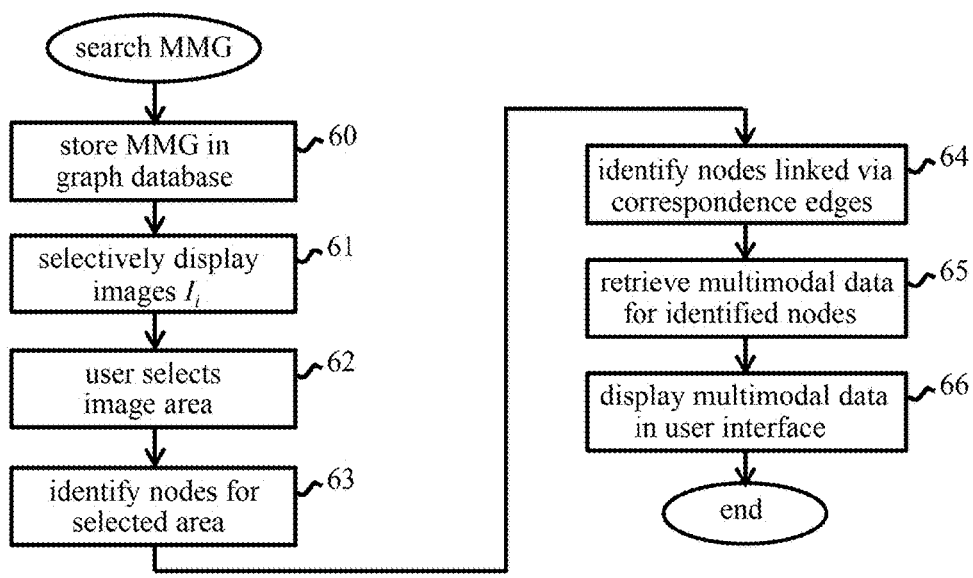
FIG. 12 indicates steps of another processing operation for multimodal graphs in an embodiment of the system.

MMG processor 27 may also store the multimodal graph in a graph database structure in system memory 21, and provide a search engine 29 for handling search queries for this database. In response to user input of a search query, e.g., via a GUI (graphical user interface) deployed at UI 36, search engine 29 then retrieves multimodal data relating to the search query from the graph database and displays the search results via the GUI. A particularly advantageous implementation here is illustrated in FIG. 12. Step 60 represents storage of the multimodal graph in a graph database. As indicated at step 61, MMG processor 27 can, under user control, selectively display the different-modality images $I_i$ in the GUI. In response to user-selection of an area of one image (e.g., by clicking on an image area in the GUI) as indicated at step 62, search engine 29 then retrieves from the graph database multimodal data relating to the selected image area. In particular, at step 63, the search engine identifies an initial set of one or more nodes, representing entities or anchor elements in the selected image area, in the anchor graph for the selected image mode. In step 64, the search engine then locates one or more (anchor and/or entity) nodes in other anchor graphs which are linked (directly or indirectly) via correspondence edges to the initial set of nodes in the multimodal graph. In step 65, multimodal data, comprising the attribute data for all identified nodes, is then retrieved from the graph database and displayed to the user in step 66. This data may be displayed along with relevant areas of all image modes to indicate correspondences between the different images.

Figure 13:
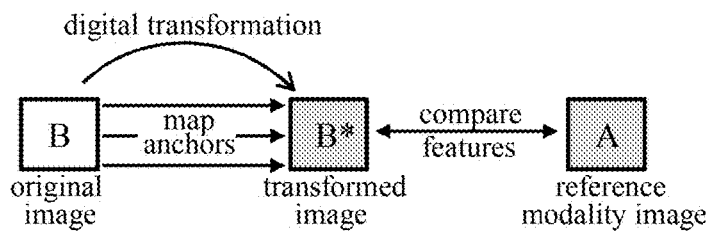
FIG. 13 indicates operation of an embodiment using an image transformation process.

In a modification to the above embodiments, correspondence edges may be defined in the multimodal graph based on analysis of digitally transformed images. The FIG. 13 schematic illustrates basic principles here. For two or more different-modality images (here two images A and B), one image modality (here of image A) is selected as a reference modality based on task-specific selection criteria. Each non-reference-modality image (here B) is then digitally processed to obtain a transformed image (B*) in the reference modality. Known image-transformation techniques can be employed here to adjust features, such as color and tone of different areas, according to appearance of images in the reference modality. Anchor elements for the non-reference modality image B are then mapped to its transformed image B* in the reference modality. A set of anchor attributes is then determined for each anchor element in the reference-modality image B*. Correspondence edges in the multimodal graph can then be defined (wholly or partially) based on these attributes. Since features appear visually more similar in the reference modality images, this facilitates comparison of features for definition of correspondence edges.

It will be seen that the above techniques offer context-aware evaluation of multimodal tissue images for improved medical diagnosis. The multimodal graph provides a compact representation of multimodal image data which retains all original information and can be readily scaled to accommodate even whole-slide images.

It will be appreciated that numerous changes and modifications can be made to the exemplary embodiments described. By way of example, the evaluator (ML classifier 51) in FIG. 11 may be an ML regression model (e.g., for severity grading) in other embodiments. Various other graph processing models, such as other GNN architectures, can be envisaged for ML model 28. Also, while cell-level entity graphs are described above, entity graphs can be constructed for supra-cellular structures, and may be hierarchical graphs in some embodiments. In particular, image processor 23 may detect biological entities at a plurality of hierarchy levels in the image, e.g., at each of a plurality of different magnification levels in a WSI. An entity subgraph can then be generated for each hierarchy level generally as described above. Each entity subgraph then comprises entity nodes, representing respective biological entities detected at that hierarchy level, interconnected by edges representing interactions between entities represented by those nodes. The final entity graph is then generated as a hierarchical graph in which nodes of different entity subgraphs are interconnected by edges ("hierarchical edges") representing hierarchical relations between nodes of the entity subgraphs. Anchors may comprise entities represented by nodes in subgraphs for one or more hierarchy levels, and/or landmarks, regions, grid areas defined for the respective image, etc. from one or more images at different magnification levels of a WSI. In general, relevant biological entities can be detected based on pathological prior knowledge for a given evaluation task.

The techniques be described can be applied to digital images other than pathology images, including medical images such as MRI and CT images, or any combination of different image modalities.

In general, where features are described herein with reference to a method embodying the invention, corresponding features may be provided in a system/computer program product embodying the invention, and vice versa.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for processing a plurality of different-modality digital images of tissue, the method comprising:
   for each image, detecting biological entities in the image and generating an entity graph comprising entity nodes, the entity nodes representing respective biological entities, interconnected by edges representing interactions between the biological entities represented by the entity nodes;
   selecting, from each image, a set of anchor elements comprising elements corresponding to anchor elements of at least one other image, and generating an anchor graph in which anchor nodes, representing the respective anchor elements, are interconnected with the entity nodes of the entity graph for the image by the edges indicating relations between the entity nodes and the anchor nodes;
   generating a multimodal graph by interconnecting the anchor nodes of the anchor graphs for different images via correspondence edges indicating correspondence between the anchor nodes; and
   processing the multimodal graph to output multimodal data, derived from the plurality of images, for medical evaluation.

2. The method as claimed in claim 1, wherein at least one of the different-modality images comprises a digital pathology image of a tissue specimen.

3. The method as claimed in claim 1, wherein the different-modality images comprise digital pathology images of a tissue specimen with different stains.

4. The method as claimed in claim 3, wherein the digital pathology images comprise whole-slide images.

5. The method as claimed in claim 1, wherein the anchor elements comprise elements selected from:
the biological entities;
salient regions in the image;
landmarks in the image;
superpixels derived for the image; and
grid areas defined for the image.

6. The method as claimed in claim 1, wherein the entity graph includes, for each entity node, a set of attributes of the biological entity represented by that node.

7. The method as claimed in claim 1, wherein the anchor graph includes, for each anchor node, a set of attributes associated with the corresponding anchor element, the method including defining the correspondence edges in dependence on attributes of the anchor elements for the different images.

8. The method as claimed in claim 7, further comprising defining the correspondence edges between anchor nodes in dependence on similarity of the attributes for those anchor nodes.

9. The method as claimed in claim 1, further comprising defining the correspondence edges between anchor nodes in dependence on graph edit distance between subgraphs, depending from those anchor nodes, in the anchor graphs.

10. The method as claimed in claim 1, further comprising defining the correspondence edges by supplying the anchor graphs for the images to a machine learning model pre-trained to define the correspondence edges between anchor nodes of such anchor graphs.

11. The method as claimed in claim 1, further comprising:
selecting a reference modality for the images;
digitally transforming each non-reference-modality image into a transformed image in the reference modality;
mapping anchor elements for each non-reference-modality image to its respective transformed image in the reference modality;
determining for each anchor element in images in the reference modality, a set of attributes associated with that element in the reference modality image; and
defining the correspondence edges in dependence on attributes of anchor elements determined from the reference-modality images.

12. The method as claimed in claim 1, further comprising defining the edges interconnecting the anchor nodes and the entity nodes in the anchor graph in dependence on at least one of positional and hierarchical relations between the anchor elements and entities represented thereby.

13. The method as claimed in claim 1, wherein the biological entities comprise entities selected from nuclei, cells, tissue parts, glands, and whole tissues.

14. The method as claimed in claim 1, including defining the edges in the entity graph representing interactions between entities in dependence on at least one of distance between the entities and predetermined biological interactions between the entities.

15. The method as claimed in claim 1, further comprising, for each image:
detecting the biological entities at a plurality of hierarchy levels in the image;
generating, for each hierarchy level, an entity subgraph comprising the entity nodes, representing respective biological entities detected at that hierarchy level, interconnected by the edges representing interactions between entities represented by those nodes; and
generating the entity graph as a hierarchical graph in which nodes of different entity subgraphs are interconnected by hierarchical edges representing hierarchical relations between nodes of the entity subgraphs.

16. The method as claimed in claim 1, further comprising processing the multimodal graph in a pre-trained machine learning model adapted to output multimodal result data corresponding to a medical diagnosis for the tissue.

17. The method as claimed in claim 1, further comprising:
storing the multimodal graph in a graph database;
in response to input of a search query via a user interface, retrieving from the graph database multimodal data relating to the search query; and
displaying the multimodal data via the user interface.

18. The method as claimed in claim 17, further comprising:
selectively displaying the different-modality images via the user interface; and
in response to user-selection, via the interface, of an area of one image, retrieving from the graph database multimodal data comprising data associated with at least one node, representing an entity or anchor element in the area, in the anchor graph for that image and data associated with one or more nodes, linked via the correspondence edges to the at least one node, of other anchor graphs in the multimodal graph.

19. A computing system for processing a plurality of different-modality digital images of tissue, the system comprising:
memory for storing the different-modality images; and
one or more processors coupled to the memory, the one or more processors configured to execute:
image processing logic adapted to detect biological entities in each image;
entity graph logic adapted, for each image, to generate an entity graph comprising entity nodes, the entity nodes representing respective biological entities, interconnected by edges representing interactions between the biological entities represented by the entity nodes;
anchor graph logic adapted to select, from each image, a set of anchor elements comprising elements corresponding to the anchor elements of at least one other image, and to generate an anchor graph in which the anchor nodes, representing the respective anchor elements, are interconnected with the entity nodes of the entity graph for the image by the edges indicating relations between the entity nodes and the anchor nodes;
multimodal graph logic adapted to generate a multimodal graph by interconnecting the anchor nodes of the anchor graphs for different images via correspondence edges indicating correspondence between the anchor nodes; and
graph processing logic adapted to process the multimodal graph to output multimodal data, derived from the plurality of images, for medical evaluation.

20. A computer program product for processing a plurality of different-modality digital images of tissue, the computer program product comprising a computer readable storage medium having program instructions embodied therein, the program instructions being executable by a computing system to cause the computing system to:
for each image, detect biological entities in the image and generate an entity graph comprising entity nodes, the entity nodes representing the respective biological entities, interconnected by edges representing interactions between entities represented by the entity nodes;

select, from each image, a set of anchor elements comprising elements corresponding to anchor elements of at least one other image, and generate an anchor graph in which anchor nodes, representing the respective anchor elements, are interconnected with the entity nodes of the entity graph for the image by the edges indicating relations between the entity nodes and the anchor nodes;

generate a multimodal graph by interconnecting the anchor nodes of the anchor graphs for different images via correspondence edges indicating correspondence between the anchor nodes; and process the multimodal graph to output multimodal data, derived from the plurality of images, for medical evaluation.

* * * * *